(12) United States Patent
Merinville et al.

(10) Patent No.: US 11,213,479 B2
(45) Date of Patent: Jan. 4, 2022

(54) COSMETIC COMPOSITION COMPRISING A PASSIONFLOWER EXTRACT AND EDELWEISS CELLS, AND USES

(71) Applicant: SOCIETE DE RECHERCHE COSMETIQUE S.A.R.L., Luxembourg (LU)

(72) Inventors: Eve Merinville, Luxembourg (LU); Judith Elkaim, Metz (FR)

(73) Assignee: SOCIETE DE RECHERCHE COSMETIQUE S.A.R.L., Luxembourg (LU)

( * ) Notice: Subject to any disclaimer, the term of this patent is extended or adjusted under 35 U.S.C. 154(b) by 0 days.

(21) Appl. No.: 16/535,807

(22) Filed: Aug. 8, 2019

(65) Prior Publication Data

US 2020/0069565 A1  Mar. 5, 2020

(30) Foreign Application Priority Data

Aug. 10, 2018  (LU) ........................................ 100904

(51) Int. Cl.

| | | |
|---|---|---|
| *A61K 8/9789* | (2017.01) | |
| *A61K 8/34* | (2006.01) | |
| *A61K 8/362* | (2006.01) | |
| *A61K 8/365* | (2006.01) | |
| *A61K 8/37* | (2006.01) | |
| *A61K 8/44* | (2006.01) | |
| *A61K 8/49* | (2006.01) | |
| *A61K 8/73* | (2006.01) | |
| *A61K 8/81* | (2006.01) | |
| *A61Q 17/04* | (2006.01) | |
| *A61Q 19/08* | (2006.01) | |

(52) U.S. Cl.
CPC ............ *A61K 8/9789* (2017.08); *A61K 8/345* (2013.01); *A61K 8/362* (2013.01); *A61K 8/365* (2013.01); *A61K 8/37* (2013.01); *A61K 8/375* (2013.01); *A61K 8/442* (2013.01); *A61K 8/498* (2013.01); *A61K 8/73* (2013.01); *A61K 8/8147* (2013.01); *A61Q 17/04* (2013.01); *A61Q 19/08* (2013.01)

(58) Field of Classification Search
CPC .................................................... A61K 8/9789
See application file for complete search history.

(56) References Cited

U.S. PATENT DOCUMENTS

| | | | |
|---|---|---|---|
| 2019/0000902 A1* | 1/2019 | Leclere-Bienfait | .... A61Q 17/00 |
| 2019/0209631 A1* | 7/2019 | Leclere-Bienfait | .... A61K 31/56 |

FOREIGN PATENT DOCUMENTS

| | | | | |
|---|---|---|---|---|
| EP | 2 319 914 | | 5/2011 | |
| FR | 3 045 380 | | 6/2017 | |
| FR | 3045380 | A1 * | 6/2017 | ............. A61K 8/368 |
| KR | 101740097 | B1 * | 5/2017 | |

OTHER PUBLICATIONS

Database GNPD [Online] MINTEL; Mar. 2, 2016 anonymous: "Alp-Cells Repair Unique Global Anti-Aging Cream".
Database GNPD [Online] MINTEL; May 23, 2016 anonymous: "Day Cream for Dry Skin", extrait de www.gnpd.oom.
Database GNPD [Online] MINTEL; Jun. 5, 2017 (Jun. 5, 2017), anonymous: "Facial Cream".
Database GNPD [Online] MINTEL; Apr. 7, 2017 anonymous: "Antioxidant Moisturizer with White Tea".
International Search Report dated Dec. 18, 2018.
Database Mintel [online] "Décolift cream".
Database GNPD Mintel [online] "Nourish+Protect antioxidant moisturer".

* cited by examiner

*Primary Examiner* — Gina C Justice
(74) *Attorney, Agent, or Firm* — Ipsilon USA, LLP (57) ABSTRACT

The present invention relates to a novel cosmetic or dermatological composition for topical or oral use, comprising at least one passionflower extract, at least edelweiss callus cells, and at least one physiologically acceptable support, to a non-therapeutic cosmetic skin treatment process using such a cosmetic composition, and also to the non-therapeutic use of such a cosmetic composition for protecting the skin against environmental attack, preventing, retarding and/or combating the signs of ageing of the skin.

15 Claims, 3 Drawing Sheets

COSMETIC COMPOSITION COMPRISING A PASSIONFLOWER EXTRACT AND EDELWEISS CELLS, AND USES

RELATED APPLICATION

This application claims the benefit of priority from Luxembourg Patent Application No. LU 100904, filed on Aug. 10, 2018, the entirety of which are incorporated by reference.

FIELD OF THE INVENTION

The present invention relates to the general technical field of cosmetic or dermatological products for topical or oral use, which may be used notably on the skin.

DESCRIPTION OF THE RELATED ART

More precisely, the present invention relates to a novel cosmetic composition for topical application comprising at least one passionflower extract, edelweiss callus culture cells and/or an extract of edelweiss callus culture cells and at least one physiologically acceptable support, to a non-therapeutic cosmetic skin treatment process using such a cosmetic composition, and also to the non-therapeutic use of such a cosmetic composition for preventing and/or retarding the signs of ageing of the skin.

The skin is a true organ comprising several integrated layers, going from the surface layer, the epidermis, down to the deepest layers, the dermis and the hypodermis, and each of these layers has specific properties enabling the whole to react and to adapt to the conditions of its environment.

The epidermis is mainly composed of keratinocytes (90% of the epidermal cells) which synthesize keratin, melanocytes (2% to 3% of the epidermal cells) responsible for the pigmentation of the skin, and Langerhans cells which play an immunological role. The epidermis, the thickness of which is variable according to the different parts of the body, constitutes the outer layer of the skin and, consequently, it plays a fundamental role for ensuring protection and maintenance of good trophicity. This is why many compositions have been developed for protecting it, notably against environmental attack.

The dermis is the thickest layer, rich in nerves, blood vessels and sweat glands, and is mainly composed of collagen, elastin and proteoglycans. These three types of molecules are synthesized by the dermal fibroblasts. Collagen fibres, which represent 70% of the dry weight of the dermis, provide the skin with mechanical strength and texture, elastin is responsible for the elasticity, and the proteoglycans play a major role in structuring and moisturizing the skin. Other cells, such as macrophages and leukocytes, are also present in the dermal layer.

The hypodermis, which is the deepest layer of the skin, contains adipocytes which produce lipids so that the subcutaneous tissue manufactures a fatty layer protecting the muscles, bones and internal organs against impacts.

Ageing of the skin may be intrinsic or extrinsic, i.e. it may be caused by the environment, including climatic attacking factors, which may notably contribute towards accelerating the degradation of the dermal collagen. In particular, exposure to sunlight, temperature variations and pollution play a harmful role on the skin by generating free radicals, which are reactive oxygen derivatives (or ROS, "reactive oxygen species") such as the superoxide anion ($O_2^{\cdot-}$). Radical-mediated attack initiates chain reactions which stop only when two free radicals become mutually inactivated. In particular, free radicals give rise to oxidative stress which impairs the membrane lipids of the skin cells and the cells themselves, notably in the mitochondrial DNA and the mitochondria, causing premature and/or accelerated ageing of the skin. Specifically, the mitochondrion acts within the cell as an energy station by producing ATP. Reducing its activity, notably associated with its capacity to respond to oxidative stress in the form of ROS, is directly connected to the ageing process and to the symptoms of age.

The aerobic body fortunately has an efficient system for defending against oxidative stress. Specifically, many natural antioxidants (enzymes and vitamins) with radical-scavenging properties are either produced by the body or taken from the diet. Thus, vitamin C inhibits free radicals within the cell, whereas vitamin E and carotenoids play the same role in the cell membrane.

Cellular ageing may be defined as the gradual loss of the body's capacity to maintain the equilibrium between free radicals and antioxidants. In the skin, free radicals bring about the marks of the passage of time: withering of the skin, cutaneous slackening, wrinkles, pigmentation marks, etc., and also skin cancers.

It is thus important to protect skin cells against the harmful effects of environmental attack, and in particular the oxidative stress generated notably by UV rays and pollution, in order to prevent and/or retard the appearance of signs of ageing of the skin such as wrinkles and fine lines.

The introduction of antioxidants into many cosmetic compositions for topical application such as creams, milks, sera, etc. is for the purpose of combating the harmful effects of these free radicals.

It is thus possible to overcome this imbalance by applying to the skin cosmetic compositions having radical-scavenging properties in order to combat the appearance of the signs of ageing.

Products of natural origin or containing natural compounds are moreover increasingly appreciated by cosmetic product consumers. This is why an ever-increasing number of products containing natural substances or substances of natural origin and having radical-scavenging properties are found on the cosmetic products market.

Such compositions conventionally contain at least one antioxidant substance, in particular complex molecules of plant origin, for instance polyphenols, flavonoids, anthocyanosides, carotenoids, etc.

However, despite the diverse compositions available, there is still a need to have available novel alternative topical compositions that can efficiently combat the effects of ageing of the skin, and notably topical compositions based on suitable plant extracts preferentially originating from plants that are known for their favourable properties.

Passionflower, of the Passifloraceae family, is a hardy medicinal plant used in infusions for its calmative and sedative effect. It comprises several hundred species, some of which, such as *Passiflora edulis* and *Passiflora ligularis*, are known to give edible fruit (passionfruit and granadilla). Cosmetic compositions intended for combating ageing of the skin and containing oils rich in essential fatty acids and also a passionflower extract are described in patent EP 1 002 524. Patent application JP 2002 332224 describes a cosmetic composition for combating ageing of the skin, containing a passionflower extract as compound for eliminating superoxide ions and an additive chosen from moisturizers, antioxidants, cell activators, bleaching agents and sunscreens. Finally, patent EP 2 291 173 describes a cosmetic or dermatological composition comprising in combination a passionflower extract and an *Anchusa arvensis* extract, which affords a skin-decontracting effect and is capable of combating muscular contractions, in particular for preventing or reducing expression wrinkles resulting from uncontrolled facial muscle contractions.

Objects and Summary:

Edelweiss (in particular *Leontopodium alpinum*), is a plant of the Asteraceae (formerly Compositae) family. It is one of the most famous of mountain plants, partly owing to its rarity. Edelweiss is cultivated in Switzerland and is used by the cosmetics industry for its anti-inflammatory properties. Moreover, patent FR 3031454 describes the use of undifferentiated or de-differentiated *Leontopodium alpinum* cells obtained via an in vitro cell culture process, for a cosmetic treatment for restoring the homeostasis of aged skin cells and for increasing their metabolic activity.

Now, the studies performed by the Applicant have shown that the combination of a passionflower extract and of edelweiss callus culture cells and/or of an extract of edelweiss callus culture cells has, unexpectedly, synergistic antioxidant activity in the presence of an oxidative stress, making this combination particularly useful as an ingredient in a cosmetic composition intended for protecting the skin and for preventing the signs of ageing of the skin.

A first subject of the present invention is thus a cosmetic composition for topical application, comprising:
 at least one passionflower extract, and
 at least edelweiss callus culture cells and/or at least one extract of edelweiss callus culture cells, and
 at least one physiologically acceptable support.

Preferably, the edelweiss callus culture cells may be whole cells. In other words, the whole cells are advantageously non-lysed cells.

Thus, said cosmetic composition may comprise at least whole edelweiss callus culture cells and/or at least one extract of whole edelweiss callus culture cells.

The term "extract of whole edelweiss callus culture cells" means an extract in which the whole cells have notably been homogenized at high pressure to break the cell aggregates, and/or lyophilized.

Such a cosmetic composition has excellent radical-scavenging properties, these properties being usable in cosmetics for skincare, more particularly for protecting the skin against environmental attack, in particular the harmful effects of UV rays or of pollution, and for preventing the signs of ageing of the skin.

In particular, the tests performed by the Applicant have shown that the combination of a passionflower extract, in particular from *Passiflora incarnata*, and of an extract of edelweiss callus culture cells, in particular from *Leontopodium alpinum*, makes it possible to reduce the level of intracellular oxidation under oxidative stress conditions on human fibroblasts and that this activity is manifested synergistically in the tested concentration range.

A second subject of the invention is thus also a non-therapeutic cosmetic process for caring for the skin, notably for protecting the skin against environmental attack, preventing, retarding and/or combating the signs of ageing of the skin, which consists in applying to the concerned areas of the skin at least one cosmetic composition for topical application as defined above in the first subject of the invention, i.e. a topical cosmetic composition comprising:
 at least one passionflower extract, and
 at least edelweiss callus culture cells and/or at least one extract of edelweiss callus culture cells, and
 at least one physiologically acceptable support.

Preferably, the edelweiss callus culture cells may be whole cells. In other words, the whole cells are advantageously non-lysed cells.

Thus, said cosmetic composition may comprise at least whole edelweiss callus culture cells and/or at least one extract of whole edelweiss callus culture cells.

The term "extract of whole edelweiss callus culture cells" means an extract in which the whole cells have notably been homogenized at high pressure to break the cell aggregates and/or lyophilized.

Finally, a third subject of the invention is the non-therapeutic use of a cosmetic composition for topical application as defined above according to the first subject of the invention, i.e. comprising:
 at least one passionflower extract, and
 at least edelweiss callus culture cells and/or at least one extract of edelweiss callus culture cells, and
 at least one physiologically acceptable support for protecting the skin against environmental attack, preventing, retarding and/or combating the signs of ageing of the skin.

Preferably, the edelweiss callus culture cells may be whole cells. In other words, the whole cells are advantageously non-lysed cells.

Thus, said cosmetic composition may comprise at least whole edelweiss callus culture cells and/or at least one extract of whole edelweiss callus culture cells.

The term "extract of whole edelweiss callus culture cells" means an extract in which the whole cells have notably been homogenized at high pressure to break the cell aggregates and/or lyophilized.

For the purposes of the present invention, the term "physiologically acceptable support" means a support which is suitable for topical or oral use and which does not present any risk of toxicity, incompatibility, etc., when placed in contact with mucous membranes, the nails, the scalp, the hair, bodily hairs and the skin of mammals, and more particularly of human beings. This physiologically acceptable medium forms what is generally known as the excipient of the composition. According to the present invention, the physiologically acceptable support is preferably a cosmetically acceptable support.

The term "cosmetically acceptable support" means a support that is compatible with the skin and/or its integuments, which has a pleasant colour, odour and feel, and which does not cause any unacceptable discomfort (stinging, tautness or redness) during its use, notably during its application to the skin.

Among the various species of the passionflower genus that may be used in the invention, mention may be made in particular of *Passiflora incarnata, Passiflora acuminata, Passiflora alata, Passiflora antioquensis, Passiflora antiquiensis, Passiflora aurantia, Passiflora baraquiniana, Passiflora biflora, Passiflora caerulea, Passiflora capsularis, Passiflora cincinatta, Passiflora coccinea, Passiflora cumbalensis, Passiflora dictamo, Passiflora edulis, Passiflora garckei, Passiflora glandulosa, Passiflora hastata, Passiflora hircina, Passiflora laurifolia, Passiflora ligularis, Passiflora mexicana, Passiflora mixta, Passiflora mollissima, Passiflora morifolia, Passiflora multiflora, Passiflora nitida, Passiflora ornithoura, Passiflora quadrangularis, Passiflora saponaria, Passiflora suberosa, Passiflora sulcata, Passiflora tenuiloba, Passiflora tinifolia, Passiflora vitifolia, Passiflora foetida, Passiflora nigelliflora, Passiflora obscura, Passiflora gossypifolia, Passiflora grandiflora,*

*Passiflora hastada, Passiflora hibisciflora, Passiflora hirsina, Passiflora hirsuta, Passiflora hispida*, and mixtures thereof.

According to the invention, use is preferably made of the species *Passiflora incarnata*.

Use is preferably made of the aerial parts of passionflower, in particular the flowering tops of passionflower, the flowering tops comprising the flowers and young leaves of the apical part, in preference to the other parts of the plants, for preparing the extracts that may be used in the cosmetic compositions in accordance with the invention.

The passionflower extracts may be prepared from the dried and ground plant, the solids thus obtained representing about 5% of the total weight of the plant. It is possible, for example, to prepare aqueous extracts, alcoholic extracts or aqueous-alcoholic extracts, for example water-glycol or water-ethanol extracts, according to the techniques that are well known to those skilled in the art, by introducing from 0.5% to 3% by mass, preferably from 1% to 1.5% by mass, of passionflower solids into a solvent chosen from water, an alcohol and mixtures thereof. Thus, according to the invention, the amount of passionflower present in the extract used is expressed as mass of dried and ground passionflower solids introduced into the chosen extraction solvent.

The passionflower extracts that may be used according to the invention thus preferably comprise from 0.5% to 3% by mass and even more preferentially from 1% to 1.5% by mass of passionflower solids relative to the total mass of said aqueous, alcoholic or aqueous-alcoholic extract.

The amount of passionflower extract present in the cosmetic composition in accordance with the invention, expressed as mass of passionflower solids introduced into the extraction solvent, preferably ranges from about 0.001% to 0.5%, more preferentially from about 0.005% to 0.25% and even more preferentially from 0.01% to 0.05% approximately, relative to the total mass of the cosmetic composition.

Among the various species of edelweiss that may be used in the invention, mention may be made in particular of *Leontopodium alpinum, Leontopodium nivale, Leontopodium coreanum, Leontopodium discolor, Leontopodium haplophylloides, Leontopodium himalayanum, Leontopodium jacotianum, Leontopodium microphyllum, Gnaphalium leontopodium* and *Gnaphalium nivale*, and mixtures thereof.

According to a preferred embodiment of the invention, use is made of callus culture cells of *Leontopodium alpinum*.

The edelweiss callus cells are derived from the in vitro culturing of undifferentiated or de-differentiated cells, referred to hereinbelow as plant cell culture.

The in vitro cell culture methods are well known to those skilled in the art. They generally comprise the following steps:

the establishment of cell lines from calluses (masses of undifferentiated or de-differentiated cells) obtained on plant part cuttings (leaf, root, stem, buds, etc.), the selection of a cell line capable of the large-scale production of a cell biomass according to pre-established criteria (constant phenotype and optimum and constant production of chosen metabolites, capacity for proliferating), the generation of said biomass from the line thus selected, optionally with a step of elicitation, preferably at the end of the proliferation phase, treatment of the biomass thus obtained to recover the whole cells.

According to the desired form of use, said cells may then be used in whole form, optionally after high-pressure homogenization to break the cell aggregates, in lyophilized form, or may undergo a lysis step, to extract the cell content therefrom.

The amount of edelweiss callus culture cells in the cosmetic composition in accordance with the invention generally ranges from about $7 \times 10^{-4}$% to 0.3%, preferably from 0.0035% to 0.15% and even more preferentially from about 0.007% to 0.03%, said amount being expressed as mass of solids relative to the total mass of the cosmetic composition.

According to the invention, the mass ratio between the amount of passionflower extract and the amount of edelweiss callus culture cells preferably ranges from 0.3 to 6 approximately, and even more preferentially from 0.75 to 3.

According to a particularly preferred embodiment, the cosmetic composition comprises the passionflower extract in an amount of about 0.02125% by mass relative to the total mass of said composition, said amount being expressed as mass of passionflower solids introduced into the extraction solvent, and 0.014% by mass of edelweiss callus culture cells, relative to the total mass of said composition.

The cosmetic composition according to the invention may contain, besides the passionflower extract and the edelweiss callus culture cells, one or more secondary active agents which advantageously reinforce or complete its activity, and which are compatible, i.e. not liable to react with each other or to mask or limit its effects.

More particularly, the secondary active agents may be chosen, for example, from moisturizers, humectants, antioxidants, skin-protecting agents, anti-ageing active agents, agents for protecting against rays, notably UV rays, and mixtures thereof.

The moisturizers may be chosen, for example, from hyaluronic acid, pyroglutamic acid salts and copolymers, hydrogenated lecithin, urea and derivatives thereof, cholesterol, and mixtures thereof.

The humectants may be chosen, for example, from glycols, betaine, sugars and sugar derivatives, an extract of *Pseudoalteromonas* ferment, lactic acid, free amino acids, mineral salts, plant extracts, for instance of beetroot, hibiscus, the alga *Furcellaria lumbricalis*, and mixtures thereof.

The antioxidants may be chosen, for example, from tocopherol (vitamin E) and derivatives thereof and also extracts containing same; ascorbic acid (vitamin C) and derivatives thereof and also extracts containing same; phenols, polyphenols, phenolic acids, flavonoids, lignans, derivatives thereof and also extracts containing same; lipoic acid and derivatives thereof and also extracts containing same; iron and copper chelating agents; lactoferrin; coenzyme Q10, and mixtures thereof.

The skin-protecting agents may be chosen, for example, from agents for promoting the barrier function such as phospholipids, ceramides, fatty acids, honey, plant extracts such as *Samanea saman*, water hyacinth, porcelain rose, amaranthus, tara; radical scavengers; antipollution agents; anti-inflammatory agents and calmatives such as panthenol, resorcinol and derivatives, bisabolol, allantoin, madecassoside, menthol, extracts of poppy, of water lily, of camomile, of calendula, of aloe, and mixtures thereof.

Among the anti-ageing active agents, mention may be made notably of mechanical or chemical desquamating/exfoliating agents; agents for promoting the cutaneous microcirculation; depigmenting agents such as extracts of cocoa, of crocus and of tribulus; antiglycation agents; firming agents such as extracts of barbitamao or of gleditsia;

repairing agents such as extracts of camellia, of polygonum or of apple tree; decontracting agents such as extracts of blue lotus, of poppy, of mallow or of anchusa; agents for stimulating the synthesis of dermal or epidermal macromolecules and/or for preventing degradation thereof, in particular agents for stimulating fibroblast and/or keratinocyte proliferation, for instance peptides, lipopeptides and peptide derivatives, plant extracts such as extracts of araucaria, of mimosa, of marigold, algal extracts, plankton extracts; retinoids; tensioning agents based on proteins or on plant polysaccharides, and mixtures thereof.

The agents for protecting against rays, notably UV rays, may be chosen, for example, from organic screening agents and also from inorganic screening agents, and mixtures thereof.

The cosmetic compositions in accordance with the present invention may be in the presentation forms conventionally used for topical application, for example in the form of a gel, an emulsion (for example in the form of a cream or a milk), a microemulsion, a serum, an oil, a mask, a salve, an ointment, a lotion, a concentrated solution, a suspension, a foam, solid sticks, in particular protective sticks for the lips or aerosols, said presentation forms also containing excipients and supports that are common and physiologically acceptable in cosmetology.

These topical administration forms are prepared via the usual techniques, and, for example, in the case of a cream, by dispersing a fatty phase in an aqueous phase to obtain an oil-in-water emulsion, or conversely to prepare a water-in-oil emulsion.

Within the cosmetic compositions according to the invention, the passionflower extract and/or the edelweiss callus culture cells and/or one or more of the secondary active agents may also be in encapsulated form in macroparticles, microparticles or nanoparticles or in macrocapsules, microcapsules or nanocapsules. The passionflower extract and/or the edelweiss callus cells and/or one or more of the secondary active agents may be incorporated in vectors such as liposomes, glycospheres, in chylomicrons, macroparticles, microparticles or nanoparticles, and also in macrocapsules, microcapsules or nanocapsules, and may also be adsorbed onto a support chosen from powdery organic polymers, talcs, bentonites and other mineral supports.

The topical compositions according to the invention may comprise excipients that are suitable for external topical application, in particular physiologically acceptable excipients, and in particular in cosmetology. These excipients that are suitable for the formulation are well known to those skilled in the art and comprise, for example, emollients, organic solvents, chelating agents, penetrants, thickeners, fillers, emulsifying agents or surfactants, preserving agents, colorants, fragrances, and mixtures thereof.

DETAILED DESCRIPTION

Thus, these topical compositions may advantageously be used in cosmetology for prevention of the signs of ageing of the skin.

The cosmetic use of the cosmetic composition in accordance with the invention comprises all care of the skin, of mucous membranes, of the integuments and of the scalp, for example protective and tanning sun products, anti-ageing, moisturizing, anti-seborrhoeic and tonic products, products for improving the appearance of the skin, notably bleaching products, products used in parallel with antiacne treatments, products directed towards improving skin comfort, for example calmative products and/or products for combating skin redness and/or dryness.

The examples that follow illustrate the invention in greater detail without limiting its scope. In all the composition examples that follow, the parts are expressed on a mass basis, unless otherwise indicated.

EXAMPLES

The passionflower extract used in the examples illustrating the present invention is a water-glycerol extract obtained from the species *Passiflora incarnata*, notably from the flowering tops of this species.

After drying and pulverizing the plant, the extraction was performed by percolation in a proportion of 100 g of plant per 500 g of water. The aqueous extract obtained by percolation is diluted in 500 g of glycerol to constitute a water-glycerol extract that may be used in cosmetic formulation.

The extract thus obtained had the following characteristics:

| | |
|---|---|
| Passiflora incarnata (dry mass) | 1.25% |
| Water | 49.375% |
| Glycerol | 49.375% |

There is a direct equivalence between the concentration expressed as water-glycerol extract as described herein and the concentration expressed as mass of solids, with 0.0425% by mass of passionflower solids equivalent to 3.4% by mass of the extract.

The edelweiss callus culture cell extract used in the examples illustrating the invention is a water-ethanol extract obtained from the species *Leontopodium alpinum*. After plant cell culturing, the edelweiss cells in lyophilized form were dissolved in a mixture of 70% of ethanol and 30% of water, and the solution obtained was then homogenized and filtered.

The extract thus obtained had the following characteristics:

| | |
|---|---|
| Edelweiss cells (dry mass) | 21% |
| Ethanol | 55.3% |
| Water | 23.7% |

A *Leontopodium alpinum* culture cell extract is moreover sold under the trade name Majestem® by the company Sederma. More particularly, this extract is an extract of whole edelweiss callus culture cells. This product comprises, besides the *Leontopodium alpinum* callus culture cells, glycerol and xanthan gum. There is a direct equivalence between the concentration expressed as mass of solids and the concentration expressed for the commercial ingredient Majestem®, with 0.028% by mass of edelweiss callus cells equivalent to 2% by mass of Majestem®.

Example 1

Demonstration of the Antioxidant Effect of the Combination of a Passionflower Extract and of Edelweiss Callus Cells In this example, the antioxidant properties of the combination of a passionflower extract and of edelweiss callus cells at different concentrations was studied.

1.1. Test Principle

The test principle is based on measuring the degree of intracellular oxidation using a specific probe: 2',7'-dichlorodihydrofluorescein diacetate (DCFH-DA), which is an indicator that is sensitive to reactive oxygen species (ROS). DCFH-DA penetrates into the intracellular medium, where, after cleavage of the two acetate groups by the intracellular esterases, the DCFH produced accumulates in the cytosol.

The intracellular oxidation of DCFH with different reactive oxygen species (ROS) leads to the formation of a fluorescent product, 2',7'-dichlorofluorescein (DCF). The more the test sample is antioxidant, the more it will prevent the oxidation of DCFH to DCF, and the smaller will be the fluorescence signal. Conversely, if the test sample is not antioxidant, the fluorescence will develop in response to an induced oxidative stress. The untreated Negative Control makes it possible to determine the basal oxidation level of the cells. The Positive Control, treated by addition of 5 µM of a pro-oxidant compound, tert-butyl hydroperoxide (tBHP), makes it possible to model the induced oxidative stress in the absence of antioxidant.

The fluorescence intensity measurement for each test batch then makes it possible to evaluate the degree of intracellular oxidation of the skin cells subjected to an oxidative stress by addition of 5 µM of tBHP in the presence of the extracts and thus the antioxidant activity of the test extracts.

1.2. Protocol

The study was performed on normal human fibroblasts obtained from a 46-year-old woman (ATCC, CRL2106™). The fibroblasts were cultured in a glucose culture medium (DMEM medium containing 5 mM of glucose containing 10 mM of HEPES buffer and 10% of foetal calf serum), placed in an incubator at 37° C. and under an air/$CO_2$ (95%/5%) atmosphere.

24 hours before the start of the test, the fibroblasts were transferred into 96-well plates in a proportion of 20 000 cells per well and placed in contact with the treatments under study and then returned under the same culture conditions.

The treatments under study were divided into 13 batches described below, in which the concentrations are expressed as mass of passionflower (PF) and of edelweiss (EW) solids. Starting with the extracts described above, the concentration was adjusted by dilution in the same cell culture medium.

Batch 1: CONTROL (−): untreated and unstressed fibroblasts;

Batch 2: CONTROL (+): untreated and stressed fibroblasts;

Batch 3: Sole extract: fibroblasts treated with 0.010625% of passionflower (PF) solids and stressed;

Batch 4: Sole extract: fibroblasts treated with 0.02125% of passionflower (PF) solids and stressed;

Batch 5: Sole extract: fibroblasts treated with 0.0425% of passionflower (PF) solids and stressed;

Batch 6: Sole extract: fibroblasts treated with 0.007% of edelweiss (EW) callus culture cells and stressed;

Batch 7: Sole extract: fibroblasts treated with 0.014% of edelweiss (EW) callus culture cells and stressed;

Batch 8: Sole extract: fibroblasts treated with 0.028% of edelweiss (EW) callus culture cells and stressed;

Batch 9: Combined extracts: fibroblasts treated with 0.010625% of passionflower (PF) solids and 0.014% of edelweiss (EW) callus culture cells and stressed;

Batch 10: Combined extracts: fibroblasts treated with 0.02125% of passionflower (PF) solids and 0.014% of edelweiss (EW) callus culture cells and stressed;

Batch 11: Combined extracts: fibroblasts treated with 0.0425% of passionflower (PF) solids and 0.014% of edelweiss (EW) callus culture cells and stressed;

Batch 12: Combined extracts: fibroblasts treated with 0.02125% of passionflower (PF) solids and 0.007% of edelweiss (EW) callus culture cells and stressed;

Batch 13: Combined extracts: fibroblasts treated with 0.02125% of passionflower (PF) solids and 0.028% of edelweiss (EW) callus culture cells and stressed.

As indicated above, the fibroblasts of Batch 1 received no treatment and no stress (Negative control: untreated, unstressed), whereas the fibroblasts of Batch 2 underwent an oxidative stress by addition of 5 µM of tBHP (Positive control: sole stress).

For each of the batches 3 to 13, the fibroblasts were exposed simultaneously to the indicated amounts of each of the extracts and also to the treatment by addition of 5 µM of tBHP for inducing the oxidative stress.

On conclusion of the 24 hours of treatment, the probe DCFH-DA was added to each of the wells, and the plates were again incubated at 37° C. for 30 minutes. 10 µl of hydrogen peroxide ($H_2O_2$) were moreover added to certain wells in order to check the response and the absence of saturation of the probe. The cells were then washed twice with a PBS (phosphate buffered saline) buffer solution, and the fluorescence was then measured using a spectrofluorimeter (CLARIOstar, BMG LABTEK). In a second stage, normalization of the optical density was performed by staining the cells with crystal violet solution.

1.3. Data Analysis

For all the batches (Batches 1 to 13), the percentage of measured activity of the batch relative to the basal level of the cells represented by the Negative Control (Batch 1) is calculated according to formula (1) below:

$$\% \text{ACT}m \text{ Batch } N = 100 * \text{ROS Value Batch } N / \text{ROS Value NegCtrl} \qquad (1)$$

in which:

% ACTm Batch N is the percentage of measured activity for each batch

ROS Value Batch N is the ROS value measured for each batch

ROS Value NegCtrl is the ROS value measured for the Negative Control (Batch 1).

For each combination (Batches 9 to 13), the theoretical activity equivalent to the cumulative of the effects of the two compounds in the presence of stress is then evaluated. For this, the contribution of each of the two compounds alone at the three test concentrations in the presence of stress (Batches 3 to 8) relative to the level observed for the stress alone (Positive Control—Batch 2) is first calculated according to formula (2) below for the passionflower (PF) extract:

$$\text{Contrib PF [conc } x] = \text{ROS Value PF [conc } x]/\text{ROS Value PosCtrl} \quad (2)$$

in which:
Contrib PF [conc x] is the contribution of the passionflower extract at the concentration x,
ROS Value PF [conc x] is the ROS value measured for the batch treated with the passionflower extract at the concentration x,
ROS Value PosCtrl is the ROS value measured for the Positive Control (Batch 2);
and according to formula (3) below for the edelweiss (EW) callus culture cells:

$$\text{Contrib EW [conc } y] = \text{ROS Value EW [conc } y]/\text{ROS Value PosCtrl} \quad (3)$$

in which:
Contrib EW [conc y] is the contribution of the edelweiss callus culture cells at the concentration y,
ROS Value EW [conc y] is the ROS value measured for the batch treated with the edelweiss callus culture cells at the concentration y,
ROS Value PosCtrl is the ROS value measured for the Positive Control (Batch 2).

For each combination tested, the theoretical activity should be equivalent to the cumulative of the contributions of each sole compound at the concentration used in the combination, relative to the activity of the stress alone (Positive Control—Batch 2). The percentage of theoretical activity for the combinations is thus calculated according to formula (4) below:

$$\% \text{ ACT}th \text{ Combi PF [conc } x] \text{ EW [conc } y] = \% \text{ ACT}m \text{ PosCtrl} \ast \text{Contrib PF [conc } x] \ast \text{Contrib EW [conc } y] \quad (4)$$

in which:
% ACTth Combi PF [conc x] EW [conc y] is the percentage of theoretical activity of the combination of the passionflower extract tested at the concentration x and of the edelweiss callus culture cells at the concentration y,
% ACTm PosCtrl is the percentage of measured activity for the Positive Control,
Contrib PF [conc x] and Contrib EW [conc y] are as defined above for formula (2) and formula (3).

The calculated theoretical activities were compared with the measured activities for each of the combinations tested in the presence of stress, with the values for the sole extracts and with the values for the Negative Control and Positive Control conditions.

4.4. Results

The results are reported in tables I and II below:

TABLE I

| Batches | Negative control (Batch 1) | Positive control (Batch 2) | PF extract alone + stress | EW extract alone + stress |
|---|---|---|---|---|
| 3 | 100% | 225% | 298% | — |
| 4 | 100% | 225% | 190% | — |
| 5 | 100% | 225% | 96% | — |
| 6 | 100% | 225% | — | 216% |

TABLE I-continued

| Batches | Negative control (Batch 1) | Positive control (Batch 2) | PF extract alone + stress | EW extract alone + stress |
|---|---|---|---|---|
| 7 | 100% | 225% | — | 234% |
| 8 | 100% | 225% | — | 197% |

TABLE II

| | BATCHES | | | | |
|---|---|---|---|---|---|
| | 9 | 10 | 11 | 12 | 13 |
| Negative control (Batch 1) | 100% | 100% | 100% | 100% | 100% |
| Positive control (Batch 2) | 225% | 225% | 225% | 225% | 225% |
| EW extract + stress | 234% | 234% | 234% | 216% | 197% |
| PF extract + stress | 298% | 190% | 96% | 190% | 190% |
| % of activity Theoretical combination | 310% | 198% | 100% | 182% | 166% |
| % of activity Measured combination | 182% | 68% | 74% | 165% | 86% |
| % of Synergy | −128% | −130% | −26% | −17% | −80% |

Figure 1:
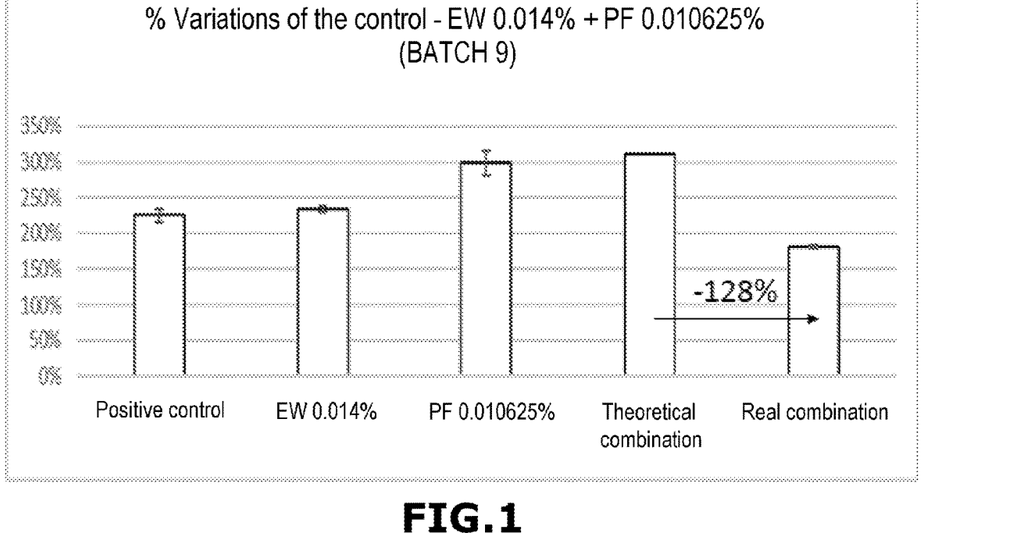
FIG. 1 is a test result of Batch 9: Combined extracts: fibroblasts treated with 0.010625% of passionflower (PF) solids and 0.014% of edelweiss (EW) callus culture cells and stressed.
Figure 2:
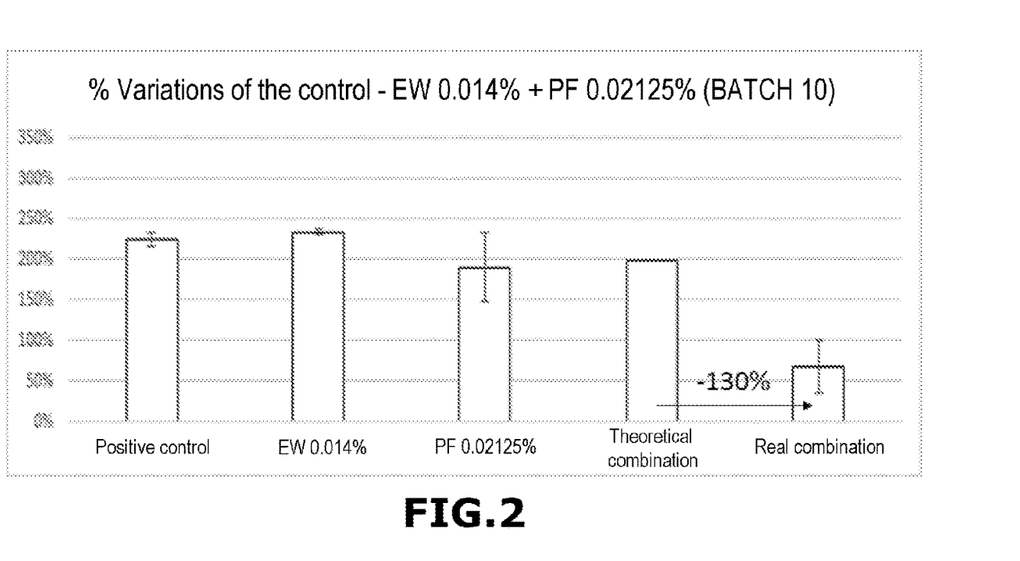
FIG. 2 is a test result of Batch 10: Combined extracts: fibroblasts treated with 0.02125% of passionflower (PF) solids and 0.014% of edelweiss (EW) callus culture cells and stressed.
Figure 3:
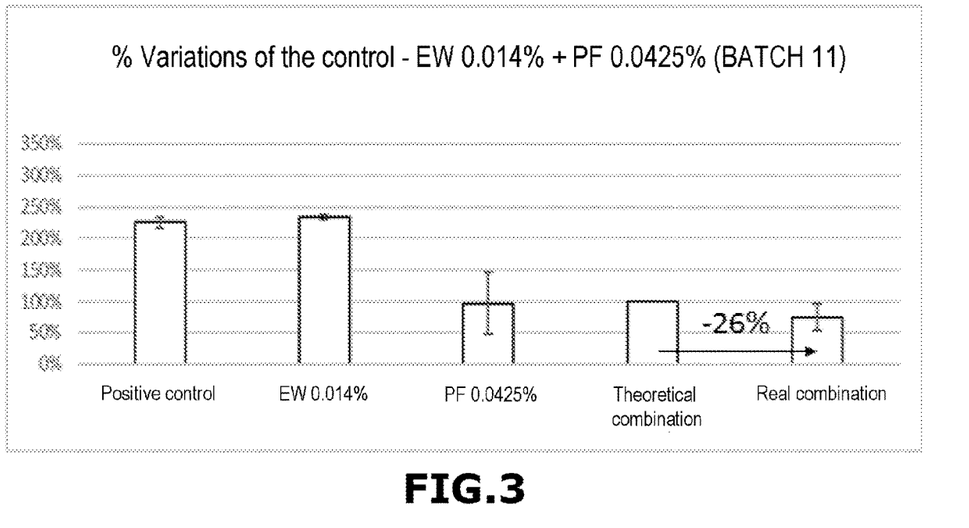
FIG. 3 is a test result of Batch 11: Combined extracts: fibroblasts treated with 0.0425% of passionflower (PF) solids and 0.014% of edelweiss (EW) callus culture cells and stressed.
Figure 4:
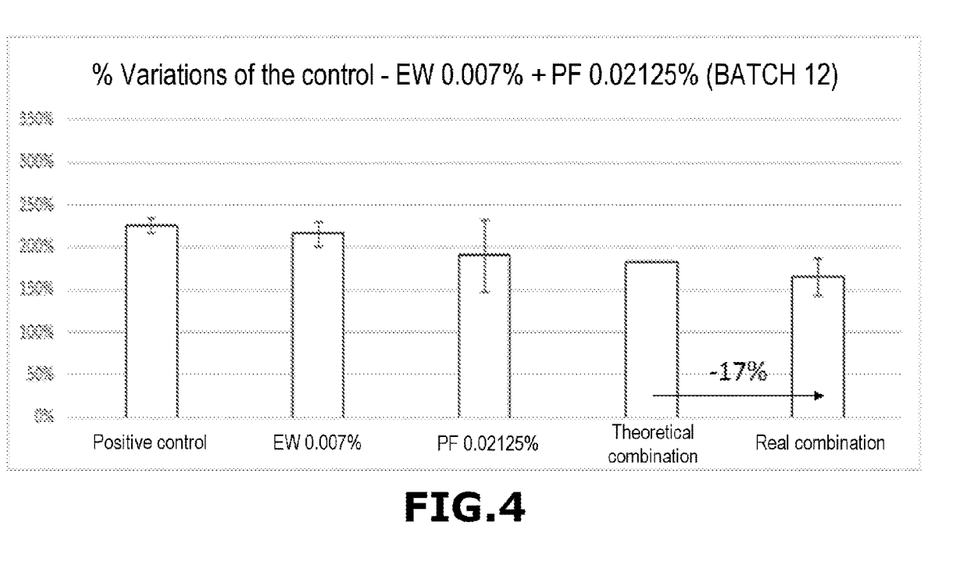
FIG. 4 is a test result of Batch 12: Combined extracts: fibroblasts treated with 0.02125% of passionflower (PF) solids and 0.007% of edelweiss (EW) callus culture cells and stressed.
Figure 5:
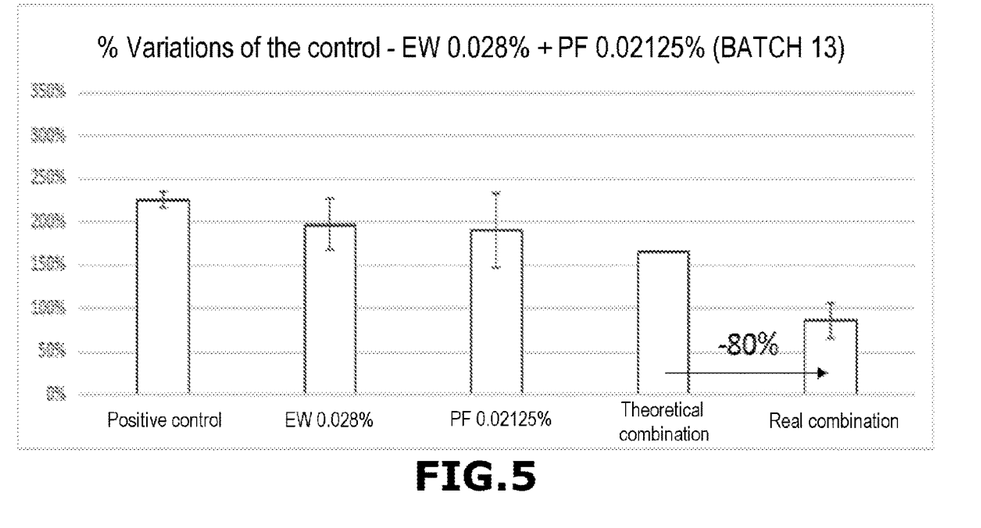
FIG. 5 is a test result of Batch 13: Combined extracts: fibroblasts treated with 0.02125% of passionflower (PF) solids and 0.028% of edelweiss (EW) callus culture cells and stressed.

The results obtained with the combinations of batches 9 to 13 are also shown in the attached FIGS. 1 to 5.

The Positive Control condition (Batch 2) shows a 125% increase in the amount of ROS produced relative to the Negative Control (Batch 1), demonstrating the pro-oxidant effect of tBHP. This increase in ROS is not significantly rectified by the compounds alone, with the exception of the composition containing the passionflower extract at 3.4%.

It may be noted that the antioxidant effect measured for all the combinations tested is higher than the theoretical effect calculated from the addition of the extracts, demonstrating a synergistic action of the two extracts when they are used in combination (FIGS. 1 to 5). This synergy is observed for all the combinations studied, for variable concentration ratios of the two extracts, as summarized in table II above.

The highest synergy is observed for the combination PF at 0.02125% and EW at 0.014% (Batch 10), which shows a reduction by a factor of 3 in the level of ROS measured in comparison with the stress condition alone (Positive Control), and also a level of ROS lower than the basal level of the cells (Negative Control), demonstrating a very strong antioxidant effect of this combination.

Example 2

Anti-Ageing Lotion

Via the usual techniques, an anti-ageing lotion in accordance with the present invention and comprising the following ingredients (in mass %) was prepared:

| | |
|---|---|
| Xanthan gum | 0.1 to 0.2% |
| Sodium gluconate | 0.1 to 0.5% |
| Water-glycerol extract of passionflower at 1.25% by mass of passionflower solids | 0.85 to 3.40% |
| *Leontopodium alpinum* culture cell extract sold under the trade name Majestem ® by the company Sederma | 0.5% to 2% |
| Glycerol | 1% to 10% |
| Denatured alcohol | 1% to 5% |
| L-Arginine | qs |
| Citric acid monohydrate | qs |
| Preserving agents | qs |
| Solubilizers | qs |
| Fragrance | qs |
| Demineralized water | qs 100.00% |

Example 3

Anti-Ageing Cream

Via the usual techniques, an anti-ageing cream in accordance with the present invention and comprising the following ingredients (in mass %) was prepared:

| | |
|---|---|
| Cetyl alcohol, glyceryl stearate, PEG-75 stearate, Ceteth-20, Steareth-20 | 1% to 7% |
| Caprylic/capric triglyceride | 1% to 15% |
| Hexyldecyl laurate, hexyldecanol | 1% to 15% |
| Carbomer | 0.2% to 1% |
| Sodium gluconate | 0.1% to 0.5% |
| Sodium polyacrylate | 0.05% to 0.2% |
| Tocopherol | 0.05% to 1% |
| Denatured alcohol | 1% to 5% |
| Water-glycerol extract of passionflower at 1.25% by mass of passionflower solids | 0.85% to 3.40% |
| *Leontopodium alpinum* culture cell extract sold under the name Majestem ® by the company Sederma | 0.5% to 2.00% |
| Sodium hydroxide | qs |
| Citric acid monohydrate | qs |
| Preserving agents | qs |
| Fragrance | qs |
| Demineralized water | qs 100.00% |

The invention claimed is:

1. A composition for topical application comprising:
   at least one passionflower extract, and
   at least edelweiss callus culture cells and/or at least one aqueous-alcoholic extract of edelweiss callus culture cells, and
   at least one physiologically acceptable support, wherein the passionflower extract is an aqueous, alcoholic or aqueous-alcoholic extract, prepared from flowering tops of passionflower.

2. The cosmetic composition according to claim 1, wherein said passionflower extract is obtained by introduction of 0.5% to 3% by mass of dried and ground passionflower solids into an extraction solvent chosen from water, an alcohol, and mixtures thereof.

3. The cosmetic composition according to claim 2, wherein the amount of passionflower extract, expressed as mass of passionflower solids introduced into said extraction solvent, ranges from 0.001% to 0.5% by mass relative to the total mass of said composition.

4. The cosmetic composition according to claim 2, wherein the amount of passionflower extract, expressed as mass of passionflower solids introduced into said extraction solvent, ranges from 0.005% to 0.25% by mass relative to the total mass of said composition.

5. The cosmetic composition according to claim 1, wherein said composition comprises edelweiss callus culture cells in an amount of from $7 \times 10^{-4}$% to 0.3%, said amount being expressed as mass of solids relative to the total mass of said composition.

6. The cosmetic composition according to claim 1, wherein said composition comprises edelweiss callus culture cells in an amount of from 0.0035% to 0.15%, said amount being expressed as mass of solids relative to the total mass of said composition.

7. The cosmetic composition according to claim 1, wherein the mass ratio between the amount of passionflower extract and the amount of edelweiss callus culture cells ranges from 0.3 to 6.

8. The cosmetic composition according to claim 2, wherein said composition comprises the passionflower extract in an amount of 0.02125% by mass relative to the total mass of said composition, said amount being expressed as mass of passionflower solids introduced into said extraction solvent, and the edelweiss callus culture cells in an amount of 0.014%, said amount being expressed as mass of solids relative to the total mass of said composition.

9. The cosmetic composition according to claim 1, wherein said composition also contains one or more secondary active agents chosen from moisturizers, humectants, antioxidants, skin-protecting agents, anti-ageing active agents, agents for protecting against rays, and mixtures thereof.

10. The cosmetic composition according to claim 1, wherein the passionflower extract and/or the edelweiss callus culture cells and/or one or more of the secondary active agents are in encapsulated form in macroparticles, microparticles or nanoparticles or in macrocapsules, microcapsules or nanocapsules, or adsorbed onto a support chosen from powdery organic polymers and mineral supports.

11. The cosmetic composition according to claim 1, wherein said composition is in the form of a gel, an emulsion, a microemulsion, a serum, an oil, a mask, a salve, an ointment, a lotion, a concentrated solution, a suspension, a foam, solid sticks or aerosols.

12. The cosmetic composition according to claim 9, wherein said secondary active agents for protecting against rays is for protecting against UV rays.

13. Non-therapeutic cosmetic process for protecting the skin against environmental attack, retarding and/or combating the signs of ageing of the skin, which includes in applying to the concerned areas of the skin at least one cosmetic composition for topical application as defined in claim 1.

14. Non-therapeutic use of a cosmetic composition for topical application as defined in claim 1, for protecting the skin against environmental attack, retarding and/or combating the signs of ageing of the skin.

15. The cosmetic composition according to claim 1, wherein the passionflower extract and/or the edelweiss callus culture cells and/or one or more of the secondary active agents are in encapsulated form in macroparticles, microparticles or nanoparticles or in macrocapsules, microcapsules or nanocapsules, or adsorbed onto a support chosen from talcs and bentonites.

* * * * *